United States Patent [19]
Goodfellow et al.

[11] Patent Number: 5,811,241
[45] Date of Patent: Sep. 22, 1998

[54] METHOD FOR PREPARING AND IDENTIFYING N-SUBSTITUED 1,4-PIPERAZINES AND N-SUBSTITUTED 1,4-PIPERAZINEDIONES

[75] Inventors: Val S. Goodfellow; Donald A. McLeod, both of Westminster; James Ivan Gerrity, Arvada; Christopher P. Laudeman, Aurora; Michael R. Burkard, Broomfield, all of Colo.

[73] Assignee: Cortech, Inc., Denver, Colo.

[21] Appl. No.: 527,407

[22] Filed: Sep. 13, 1995

[51] Int. Cl.$^6$ .................. G01N 33/53; G01N 33/566; G01N 33/543
[52] U.S. Cl. ..................... 435/7.1; 436/501; 436/518
[58] Field of Search .................. 435/7.1; 436/518, 436/531, 534; 544/44, 121, 358

[56] References Cited

U.S. PATENT DOCUMENTS 5,066,716  11/1991  Robey et al. .................. 525/54.1
5,324,483   6/1994  Cody et al. .................... 422/131

FOREIGN PATENT DOCUMENTS

WO 95/04277  2/1995  WIPO .................. G01N 33/53

OTHER PUBLICATIONS

Bunin, B. A., et al., "A General and Expedient Method for the Solid–Phase Synthesis of 1,4–Benzodiazephine Derivatives," *J. Am. Chem. Soc.*, 114, 10997–10998 (1992).

DeWitt, S. H., et al., "Diversomers: An Approach to Non-peptide, Nonologomeric Chemical Diversity", *Proc. Nat. Acad. Sci. USA*, 90, 6909–6913 (Aug., 1993).

Gallop MA, et al, (1994) Applications of combinatorial technologies to drug discovery. 1. Background and peptide combinatorial libraries. J Med.Chem. 37:1233–1251.

Gordon DW, et al, (1995) Reductive alkylation on a solid phase: Synthesis of a piperazinedione combinatorial library. Bioorg.Med.Chem. 5:47–50.

*Primary Examiner*—Lora M. Green
*Assistant Examiner*—Neal A. Musto
*Attorney, Agent, or Firm*—Cushman Darby & Cushman, IP Group of Pillsbury Madison & Sutro LLP

[57] ABSTRACT

The invention provides a method of synthesizing N-substituted 1,4-piperazines and N-substituted 1,4-piperazinediones. The invention also provides a method for synthesing combinatorial libraries of piperazine derivatives which can be assayed for biological activity in pre-specified ligand binding or enzymatic activity screens.

11 Claims, No Drawings

METHOD FOR PREPARING AND IDENTIFYING N-SUBSTITUED 1,4-PIPERAZINES AND N-SUBSTITUTED 1,4-PIPERAZINEDIONES

FIELD OF THE INVENTION

This invention relates to a method of generating large numbers of diverse non-peptide organic compounds which can be assayed for biological activity in pre-specified ligand binding or enzymatic activity screens. More specifically the diverse organic compounds formed are N-substituted 1,4-piperazines or their corresponding piperazinediones formed by "on-resin" or solid-phase cyclization of unnatural N-substituted dipeptoids. These compounds are useful in that they serve as an inexpensive source of chemical diversity to identify low molecular weight lead compounds with desired ligand affinity or enzyme inhibitory activity, which can be further optimized by combinatorial or traditional medicinal chemical methodology.

BACKGROUND OF THE INVENTION

Traditionally the most effective strategies for identifying novel non-peptide lead structures which have affinity for a targeted receptor or enzyme, which normally binds peptidic ligands, have included mass screening of diverse compounds. Mixtures of natural products, usually obtained as extracts, or chemical files of synthetic compounds are traditionally the source of diverse chemical structures for lead identification.

Often the lead compound may possess relative weak affinity for the targeted receptor or enzyme; the affinity can then be increased by systematic, empirical modification of the lead structure.

Lead compounds are found by screening of natural products obtained from plant, soil, or animal sources, or fermentation with microorganisms in diverse media. Synthetic compounds contained in historical collections of pharmaceutically interesting molecules or their synthetic precursors are also screened. Both natural and synthetic sources of chemical diversity present their own unique problems and limitations. Unfortunately natural product leads are often extremely difficult to identify, purify, and synthesize. Increasingly the use of natural products leads creates ethical dilemmas in that the organism which produces the lead compound may be rare and the discovery of a new source of biological activity may endanger the natural specie which produces the chemical, or the biome where the specie is found. Historical chemical libraries collections produced by pharmaceutical companies are often limited in diversity and scope since the original compounds were originally designed to target specific diseases or pathophysiological mediators, and more importantly diverse collections chemical files are unavailable to researchers who do not possess enormous financial resources.

Synthetic combinatorial libraries of diverse peptides have only partially answered the need for new methods to identify novel ligands for pharmaceutically interesting targets. Peptides suffer from a number of disadvantages including poor oral bioavailability, poor in vivo stability and high cost. Although a very large number of diverse peptides can be made, their structural diversity is limited to natural or readily synthesible amino acid building blocks and their linear polymeric character. The transformation of a peptide lead into an orally available, biologically stable, clinically useful drug, is an extremely time consuming and expensive research project and has met with limited success.

Recently several solid phase combinatorial approaches have been developed for creating diverse libraries based on small scaffolds which have been previously incorporated in successful drugs. These scaffolds include heterocycles such as benzodiazepines (Bunin et al., *J. Am. Chem. Soc.* 114 10997 (1992)), hydantoins (DeWitt, *Proc. Natl. Acad. Sci. USA* 90 6909 (1993)) and piperazinediones (Gordon et al., *Biorganic and Medicinal Chemistry Letters*, 5 47 (1995)) and non-heterocyclic scaffolds such as biphenyls (Pavia et al, PCT/US94/07780 (WO 95/04277). The present invention provides a method for producing 1,4-piperazine-2,5-diones or their corresponding reduced 1,4-piperazine analogs with greater potential for diversity in structure and with a chemical synthesis which offers advantages in yield, purity, cost and ease of production over known methods of producing diverse piperazinediones.

Piperazines and piperazinediones are common scaffolding structures found in a wide variety of bio-active compounds and drugs. Examples of this disclosed invention have been found to bind to human bradykinin, human neurokinin 1 and 2, human mu and kappa (animal) opioid receptors, and are expected to function as antagonists in many G-protein coupled receptors or inhibitors of many classes of enzymes.

DETAILED DESCRIPTION OF THE INVENTION

The present invention comprises a method for producing large numbers of structurally diverse piperazines and piperazindiones of the general structures illustrated below.

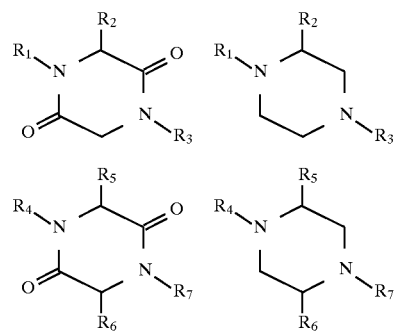

Where $R^1$ through $R^7$ are independently selected from hydrogen or C1 to C12 alkyl, C3 to C8 cycloalkyl, or alkylaryl pendant groups. The pendant groups may be substituted with guanidino, alkylguanidino, benzamidino, methoxy, ethoxy, methyl, ethyl, propyl, butyl, piperidinyl, piperazinyl, indanyl, indolyl, quinuclidinyl, hydroxyl, amino, alkylamino, aminoalkyl, biphenyl, napthyl, imidazoyl, pyridinyl, purinyl, benzoxazolyl, carboxamides, sulfonamides, carboxylates, pyrazoles, pyrimidines, fluoro, chloro, bromo, or trifluromethyl moeities.

In a preferred embodiment of the invention $R^1$ is selected from cyclohexyl, methylcyclohexyl, benzyl, substituted benzyl, phenethyl, biphenyl, benzoyl, hydrogen, methylnapthyl, indanyl, guanidinoalkyl (C2 to C8), aminoalkyl (C2 to C8), arylalkylcarbamates with alkyl chains of C2 to C8, alkanoyl (C1 to C12), and alkyl (C1 to C12) or hydrogen.

In a preferred embodiment of the invention $R^2$ is selected from benzyl, substituted benzyl, indole, methylnapthyl, cyclohexyl, methylcyclohexyl, indanyl, (C1 to C5) alkyloxyaryl, aminoalkyl (C1 to C8), guanidino alkyl (C1 to C8), alkylcarboxylic, hydroxyalkyl (C1 to C5), alkylthioalkyl, (C1 to C3) alkylbenzamidino, or hydrogen.

In a preferred embodiment of the invention $R^3$ is selected from is selected from cyclohexyl, methylcyclohexyl, benzyl, substituted benzyl, phenethyl, biphenyl, benzoyl, hydrogen, methylnapthyl, indanyl, guanidinoalkyl (C2 to C8), aminoalkyl (C2 to C8), arylalkylcarbamates with alkyl chains of C2 to C8, alkanoyl (C1 to C12), alkyl (C1 to C12), (C2 to C12)-alkylguanidinoalkyl(-C2 to C8), benzamidino, (C1 to C6) alkylbenzamidino, (C1 to C6)alkylquinuclidine, (C1 to C6) alkyl piperazine, C1 to C6 alkyl N-substituted piperazine, (C1 to C6) alkylamino piperidine, (C1 to C6) alkylamino N-substituted piperidine (C1 to C6) alkylcarboxyamidobenzamidino, (C1 to C6)alkylcarboxamidoquinuclidine, (C1 to C6) alkylcarboxamido piperazine, C1 to C6 alkylcarboxyl N-substituted piperazine, (C1 to C6) alkylcarboxamidino piperidine, or (C1 to C6) alkylcarboxamidino N-substituted piperidine, or hydrogen.

In another preferred embodiment $R^4$ and $R^7$ are independently defined as for R1; and $R^5$ and $R^6$ are independently defined as for $R^2$ or $R^3$. In this disclosure two most preferred methods for synthesizing independent purified piperazinediones and piperazines are described. A preferred method for preparing a diverse combinatorial library of piperazinediones and piperazines with several thousand discrete components from which lead bradykinin antagonist structures and other bio-active compounds with G-protein binding properties have been discovered is also disclosed.

The compounds or libraries of compounds of this invention are preferably synthesized as described in schemes I and II below. The compounds of the invention could also be synthesized by those skilled in the art by adaptation of the solid phase methodology described here to solution phase methods; such an adaptation would be considered an extension of the current invention.

A suitably N-protected α-amino acid is attached to a polymeric support using methods well known in the art. These methods include displacement of benzylic halogens to form ester linkages utilizing cesium carbonate, potassium carbonate or potassium iodide to accelerate the reaction. Ester formation can also be accomplished by the action of carbodiimide coupling reagents such as dicylohexylcarbodiimide or diisopropylcarbodiimide and a benzylic alcohol, utilizing tertirary base, with or without 4-dimethylaminopyridine as catalyst. Reagents such as BOP, HBTU, and BOP-Cl can also effectively be used to derivatize the resin. An advantage of the current invention is that the resin need not be a benzylic ester support such as Merrifield or Wang type resins, since acidolysis is not required to free the piperazinedione from the resin. The solid support may be an alkyl derivative such as polyethylene glycol or any other polymeric or discrete hydroxyl group. A very large number of suitably N-protected resin-immobilized α-amino acids are commercially available and all but the most acid sensitive of these constructs are applicable in the current invention.

Scheme I

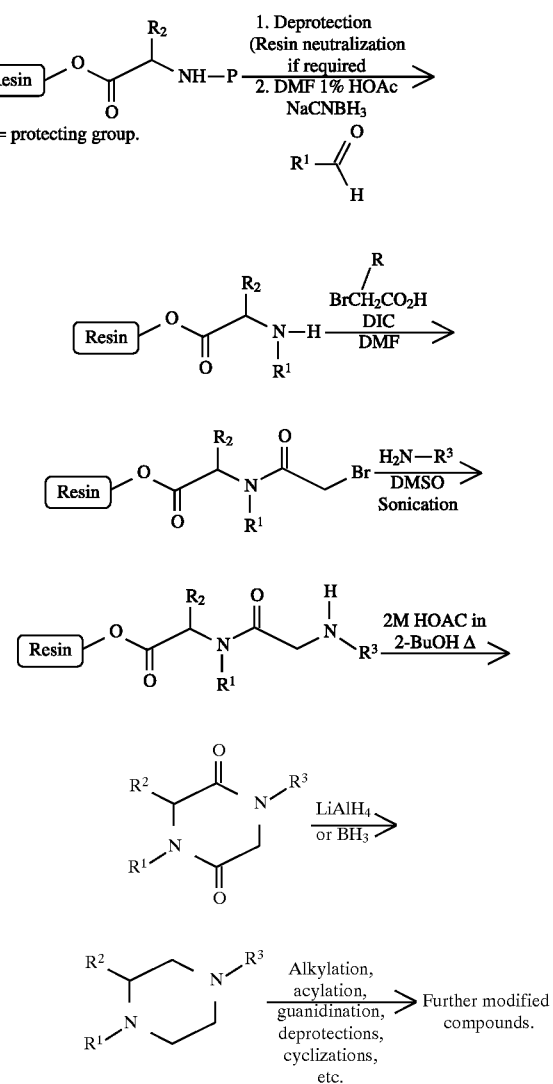

Scheme II

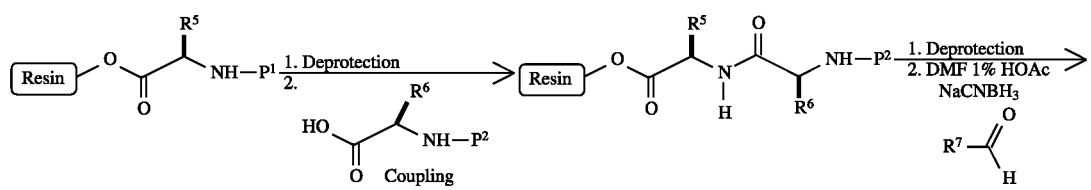

-continued
Scheme II

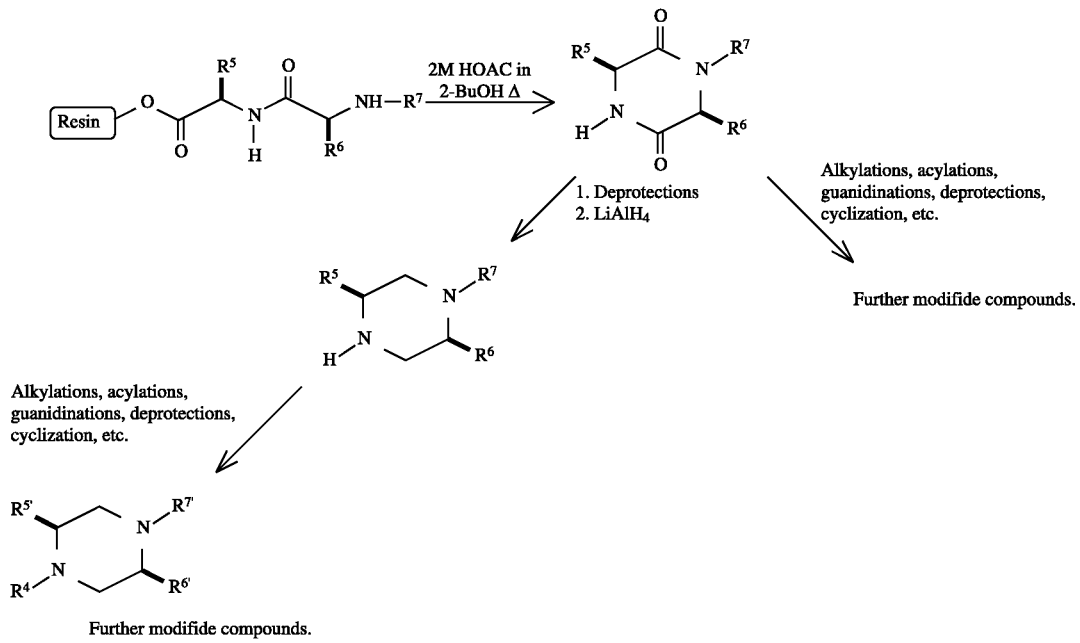

In method A, illustrated in scheme I, the resin immobilized amino acid is deprotected according to methods well known in the art. These methods may include treatment with trifluoroacetic acid for Boc-protected amino acids, treatment with secondary amines such as piperidine for Fmoc-protected amino acids or treatment with hydrogen or organic-palladium complexes for reducible protecting groups. The resulting free amino group is then reductively alkylated with a suitable adehyde, preferably by treatment with $NaCNBH_3$ in the presence of catalytic acetic acid in dimethylformamide. A number of alternative methods for accomplishing reductive amination are known in the art and include hydrogenation in the presence of soluble organic substituted metal catalysts, variously substituted borohydride reagents or the use of Lewis Acids such as $Ti(O-Pr)_4$ and sodium cyanoborohydride. The resulting secondary amine is facilely bromoacetylated with bromoacetic acid and diisopropylcarbodiimide or dicyclohexylcarbodiimide. This reaction can also be accomplished with other coupling reagents such as HBTU. The resulting bromoacetyl compound is then reacted with concentrated primary amines in a polar aprotic solvent such as DMSO to provide an N-substituted glycyl residue. The key step to the synthesis in this disclosure is the solid-phase mediated simultaneous cyclization and cleavage of the incipient dipeptoid from the solid phase resin. This is accomplished by heating in a non-reactive solvent such as 2-butanol in the presence of a catalyst such as acetic acid. The boiling point, polarity, solvent characteristics and hydroxylic character of racemic 2-butanol all contribute to the success of the cyclization method. The simultaneous cyclization and release of piperazinediones has numerous advantages:

1. Since compounds which are not dipeptoids are not released from the resin by these mild conditions, failure sequences or potential impurities are not freed from the resin to contaminate the desired piperazinediones. Crude purities, following aqueous work-up, in excess of 95% can be obtained in selected cases.

2. The mild deprotection chemistry involved allows a very large number of acid sensitive substituents and acid sensitive protecting groups to be employed, we have routinely produced diketopiperizines containing versatile protecting groups such as the Boc and Cbz group which were then removed for further modification of the molecule.

3. The reaction scheme is simple and provides compounds of superior purity without resorting to expensive and sensitive reagents such as PyBrop or its relatives or corrosive acids such as TFA; such considerations increase the propensity for the application of this method to automated reaction devices.

4. Since the cyclization/cleavage reaction is driven by high temperature and is a highly favored intramolecular formation of a piperazindione, amide bonds can be formed which are very difficult to form by alternative methods. For example the solution and solid phase formation of the dipeptoid illustrated was attempted using a number of reagents including PyBrop, the reagent of choice for the synthesis of peptoids involving couplings at hindered secondary amines and suggested for the solid-phase synthesis of piperazinedione libraries, (D. W. Gordon Biorganic and Medicinal Chemistry Letters, 5 47 (1995)) in our hands we obtained essentially none of the desired compound. Utilizing the methodology of this invention (method B) a corresponding difficult amide bond was formed very readily during the cleavage step. Consequently we believe that piperazindiones are readily available utilizing this methodology which can not be easily formed by other reported methods which involve couplings of very hindered secondary amines.

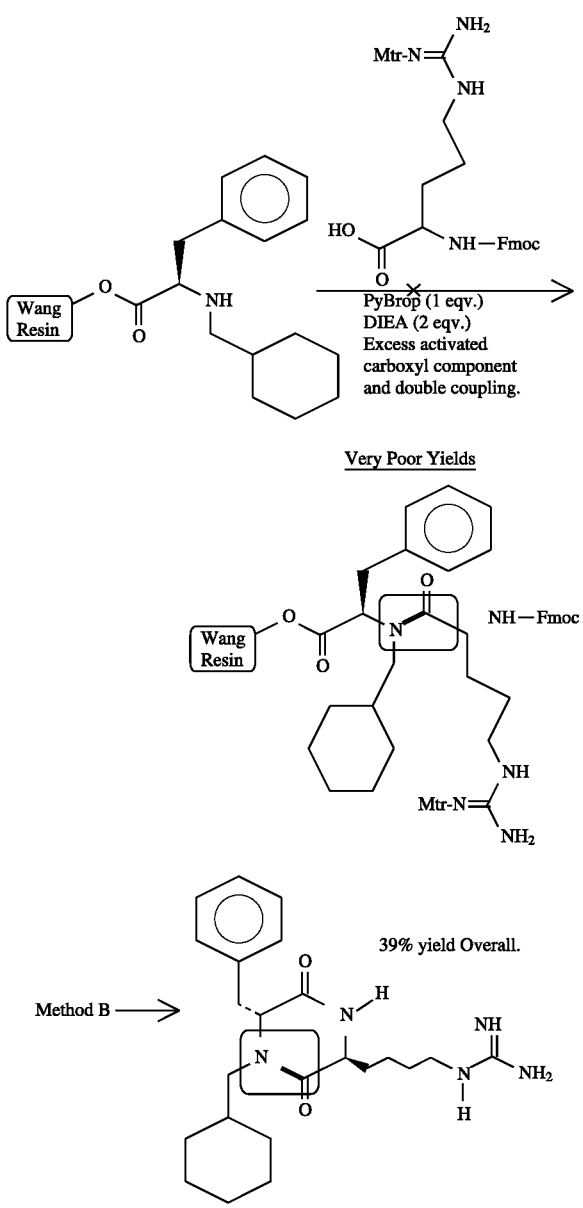

An additional advantage is accrued by the addition of the R³ substituent by displacement with a primary amines via method A. The introduction of complex groups via primary amines greatly increases the diversity of substituents for the side chain over methods which only employ aldehydes as in reductive alkylation reactions. The supply of commercial primary amines is much more diverse than less stable commercial aldehydes. A very large number of suitable primary amines are available commercially or through simple synthetic steps making an enormous number of diverse compounds possible. The geometric orientation of such N-substituted species offers increased diversity over piperazinediones obtained from simple dipeptides.

In method B a dipeptide may be synthesized on a supporting resin by methods well known in the art, deprotection of the dipeptide produces an N-terminal amine which is reductively alkylated as described in method A. Again the key step to the synthesis in this invention is the solid-phase mediated simultaneous cyclization and cleavage of the incipient dipeptoid from the solid phase resin. This is accomplished by heating at reflux in a non-reactive solvent such as 2-butanol in the presence of a catalyst such as acetic acid. As in method A a large number of additional reactions and deprotections can subsequently be carried out on the free diketopiperazines. We illustrate a number of deprotection reactions, acylations and guanidination reactions.

Piperazinediones produced by either method A or method B can be reduced to the corresponding piperazine structure by treatment with strong reducing agents such as diborane or lithium aluminum hydride.

In many instances the compounds that are produced are of high purity and may be assayed directly or they may be purified by common chromatographic techniques such as preparative reverse phase high performance chromatography or ion exchange chromatography.

In order to produce large numbers of diverse analogs, mixtures of precursor reagents may be formed which produce mixtures of compounds which differ in structure in the various side chain substitutions.

A simple method for producing mixtures of controlled content is to derivatize individual resin samples with a given amino acid substituent and then mix portions of such resins, each portion derivitized with a unique amino acid substituent. The resins are then split into aliquots and reacted with different reagents which produce a variety of substituents at one given position. Each aliquot is then split into new aliquots which are reacted with reagents which provide a variety of substituents at a new position. In the examples of this patent we illustrate this process by providing a resin mixture which is derivatized by 10 different amino acid derivatives. (This number could be much larger, but a simple example is chosen for clarity.) This resin is split into 12 aliquots. Each of 10 aliquots is reductively alkylated with a unique aldehyde. Each resulting aldehyde is split after bromoacetylation into 12 new aliquots, each of which is reacted with a unique primary amine. The resulting compound is then cyclized and each resulting mixture is split in half, half of the aliquot is then reduced with lithium aluminum hydride to provide piperazines. Two of the original aliquots are not reacted with aldehydes but are bromoacetylated, reacted with amines, cyclized, reduced to piperazines first and then acylated with either benzoic acid or dodecanoic acid. The various processes illustrated here produce a large number of mixtures of compounds, where each mixture contains at least 10 unique piperazines or piperazindiones. These mixtures are conveniently assayed by HPLC and MALDI-Mass Spectrometry, and then tested after dissolution in DMSO for activity in selected biological assays. We illustrate broad screening on a human bradykinin receptor clones. Human neurokinin type I and II receptor clones, human mu and guinea pig brain kappa opioid receptor clones. Compounds can be selected for specific identification and resynthesis on the basis of an apparent level of inhibition at a given concentration.

This process is concisely illustrated by the discovery of two bradykinin human receptor ligands as potentially pharmaceutically useful leads for the development of potent bradykinin antagonists. Screening of example combinatorial mixture 219 at an average estimated concentration of 10 uMolar produced 77% inhibition of radio-labeled bradykinin binding in the human receptor clone assay. This sample was subjected to a 5–60% CH3CN, 30 minute, then 60–90%, 15 minute gradient in water containing constant 0.1% TFA on a 25 mm reverse phase HPLC column, (10 mL/min flow rate). Fractions of approximately 10 mL were collected. Aliquots of the collected fractions were rescreened for BK binding inhibition and fraction 34 exhibited 65% inhibition. The active component of fraction 34 was identified with MALDI Mass spectrometry as example 60. This compound was resynthesized in pure form according to method A, and assayed for BK binding inhibition, an $IC_{50}$ value of 4.1 uMolar (human $BK_2$ receptor) was obtained. In an analogous fashion, combinatorial mixture example 166, exhibited 71% inhibition at an estimated average concentration of 10 uMolar. The sample was submitted to chromatography, binding assays of fractions, mass-spectrometry and the example 61 was identified as the active component and synthesized in pure form by method A. An $IC_{50}$ value of 13 uMolar (human $BK_2$ receptor) was obtained. Numerous other human receptor ligands have been identified from this single combinatorial library set.

EXAMPLES

Example 1

General Procedure for Resin Derivitization

In a solid phase peptide synthesis device (Stewart et al., Solid Phase Peptide Synthesis, Pierce Chemical Company, 1984), pre-silanized with Sigmacote, Wang peptide synthesis resin (p-benzyloxybenzyl alcohol [copolystyrene-1% divinyl benzene] resin, 0.2 to 0.80 meqv./g), 300 mg to 10 g is suspendend in DMF (10 volumes) and then the solvent is filtered away. The resin is washed two additional times with DMF. The resin is washed three times with dichloromethane, then three times with DMF. Finally the resin is suspended in DMF and allowed to mix with nitrogen bubbling for 30 to 60 minutes. In a separate flask 5 to 10 equivalents of $N^\alpha$-Fmoc-Protected amino acid is dissolved in the minimum volume of dry DMF and treated with 0.2 equivalents 4-dimethylaminopyridine, and 10 equivalents of N,N'-diisopropylcarbodiimide. The reaction is transferred to the synthesis reaction vessel containing the Fmoc-protected Amino Acid resin and the mixture is agitated for 15 hours with nitrogen bubbling. The reaction mixture is filtered away and the resin is washed sequentially, with DMF, methanol, DMF, and dichloromethane, the resin is dried in a stream of dry nitrogen, then under high-vacuum. The amount of Fmoc-amino acid added to the resin is estimated colorimetrically as follows: A 5 mg sample of the resin was suspended in 6.0 mL of DMF containing 20% piperidine. After 10 minutes of gentle agitation, the solution is decanted and the absorbance measured at 290 nM. The measured absorbance at 290 nM is multiplied by 0.2424 to yield the resin substitution in units of miliequivalents per gram of derivatized resin.

Example 2

General Procedure for Synthesis of Piperazinediones According to Method B

A. Resin Deprotection

The resin immobilized Nα-Fmoc-amino acid (side-chain $R^5$) is deprotected by reaction with 25% piperidine in DMF (~20 mL/g resin) with agitation by nitrogen bubbling for 25 minutes. The solution is filtered away and the resin is reacted again with 25% piperidine in DMF (~20 mL/g resin) with agitation by nitrogen bubbling for 25 minutes. The solution is filtered away and the resin is washed well with DMF.

B. Amino Acid Activation

Symmetrical Anhydride Method: In a separate flask 4 equivalents of the Fmoc-amino acid (side-chain $R^6$) are dissolved with warming in the minimum volume of dichoromethane containing 10% DMF, the solution is cooled to room temperature and 2 equivalents of dicyclohexylcarbodiimide are added. The reaction is stirred for 30 minutes at room temperature; the resultant dicyclohexylurea (DCU) is filtered away and the filtrate is added to the resin prepared above. The reaction mixture is agitated for 2 hours with nitrogen bubbling.

Benzotriazole Active Ester Method:

Difficult couplings such as those employing Fmoc-Ig1-OH can be accomplished by preforming the active ester by the reaction of four equivalents of the Fmoc-amino acid in DMF with four equivalents of hydroxybenzotriazole and dicyclohexyl carbodiimide. After 30 minutes (DCU) is filtered away and the reaction mixture is added to the resin as above. Similar preactivation with HBTU/HOBt and 8 equivalents diisopropylethyl-amine is acceptable for very difficult couplings.

C. Resin Deprotection

As described in step A.

D. Reductive Amination

Dried resin is suspended in DMF and agitated for 30 minutes; the DMF is filtered away and the resin is then treated with DMF (~40 mL/mmole) containing 1% acetic acid. Three equivalents of the appropriate aldehyde is added followed by 10 equivalents of sodium cyanoborohydride. The reaction is agitated by nitrogen bubbling for 6 to 24 hours. Reaction progress can be accessed by the Kaiser test (Ibid pg 76) or by HPLC analysis of a TFA cleavage reaction of a few resin beads. If incomplete reaction is obtained the reaction is filtered and resubmitted to the reductive amination conditions. When complete reductive amination is achieved the reaction mixture is filtered and washed well with DMF then dichloromethane, followed by another series of DMF washes. The resin may be dried if storage is required after the dichloromethane washes.

E. Cyclization

Dried resin or slurried aliquots are transferred to a round bottom flask or mini-reactor tube and treated with 2-butanol containing 11% (v/v) acetic acid (~5 to 10 mL/mg resin). The reaction vessel is placed in a 110° oil bath and heated at reflux under nitrogen for 48 to 72 hours. The crude piperazinedione is isolated by filtration, and washing of the resin with acetonitrile, methanol, and dichloromethane. The volatile solvents are removed by rotary evaporation. The product may be purified by HPLC chromatography. Side chain protecting groups such as Cbz and Boc are conveniently deprotected at this stage, before $LiAlH_4$ reduction. Free amino groups formed by deprotection may be acylated or guanidinated.

Example 3

General Procedure for Guanidination of Side-Chain Amino Groups Derived from N-Boc-Protected Moieties The crude diketopiperazine obtained by removal of the 2-butanol/acetic acid solution is dissolved with excess (>15 equivalents) of trifluroacetic acid as a 50% v/v solution in dichloromethane. The reaction is stirred one hour to insure removal of the side chain N-Boc protecting group. The solvent is then removed on the roto-vap. The residue is treated with dichloromethane and the solvent is again removed using rotary evaporation. The sample is again treated with dichloromethane and the solvent removed using rotary evaporation. The residues are dissolved in DMF (0.1 to 1 mL/20 mg crude product) and treated with two equivalents of pyrazole-1-carboxamidine hydrochloride (Bernatowicz et al., *J. Org. Chem.* 57 2497 (1992)) and 5 equivalents of N,N-diisopropyl-ethylamine. The reaction is stirred 6 to 24 hours and then is treated with excess TFA in dichloromethane. The solvent is evaporated and the crude product is precipitated with anhydrous diethylether and purified by reverse phase HPLC chromatography. Primary amino groups in piperazines produced by reduction of piperazinediones by $LiAlH_4$ are guanidinated using the identical procedure in DMF with two equivalents of pyrazole-1-carboxamidine hydrochloride and 5 equivalents of N,N-diisopropyl-ethylamine. The reaction is stirred 6 to 24 hours and then treated with excess TFA in dichloromethane. The solvent is evaporated and the crude product is precipitated with anhydrous diethylether and purified by reverse phase HPLC chromatography.

Example 4

General Procedure for Guanidination of Side-Chain Amino Groups Derived from N-Cbz-Protected Moieties The crude diketopiperazine obtained by removal of the 2-butanol/acetic acid solution is suspended in acetic acid (~0.5 to 1 mL/100 mg crude product) and treated with excess (>15 equivalents) of hydrobromic acid in a 30% solution in acetic acid. The reaction is stirred for 30 minutes to insure removal of the side chain N-Cbz protecting group. The crude product is precipitated by addition of anhydrous diethylether and collected by centrifugation. The primary amine (as the HBr salt) is then guanidinated as described in example 4. In general compounds are purified by reverse phase HPLC chromatography although crude puritys of 95% have been obtained.

Example 5

General Procedure for $LiAlH_4$ Reduction of Piperazinediones from Method A to Piperazines The crude piperazinedione after cyclization or side-chain deprotection is dissolved under nitrogen with 20 equivalents of a 1M $LiAlH_4$ solution; the solution is then heated at reflux under nitrogen for 24 hours. The reaction is quenched with ice and the volatiles removed by rotary evaporation. The residue is extracted with acetonitrile, filtered, acidified with TFA to ~pH 3, and the product purified by reverse phase HPLC or Sep-Pak filtration using a step gradient of 0–50% acetonitrile.

Example 6

General Procedure for $LiAlH_4$ Reduction of Piperazinediones from Method B to Piperazines The crude piperazinedione after cyclization or side-chain deprotection is dissolved under nitrogen with 20 equivalents of a 1M $LiAlH_4$ solution; the solution is then heated at reflux under nitrogen for 24 hours. The reaction is quenched with ice and the volatiles removed by rotary evaporation. The residue is extracted with acetonitrile, filtered, acidified with TFA to ~pH 3, and the product purified by reverse phase HPLC or Sep-Pak filtration using a step gradient of 0–50% acetonitrile.

Example 7

General Procedure for Acylation of Piperazines

Piperazines containing primary or secondary amines are dissolved in DMF ( 0.05 to 0.5 molar) and treated with 1.25 equivalents of the appropiate carboxylic acid, 1.25 equivalents of diisopropyl-ethylamine and 1.25 equivalents of HBTU. The reactions are agitated, stirred or sonicated for 2 to 16 hours in polypropylene conical capped tubes. Each tube is treated with a mixture of 1N NaOH and EtOAc. After vigorous mixing, the aqueous layer is removed by suction through a capillary, and the NaOH wash repeated. The organic layer is evaporated utilizing a speed-vac (high speed centrifugal vacuum evaporator) and the samples are purified by HPLC or step- wise gradient (0–80% acetonitrile in water) on a Sep-Pak column. Samples are evaporated utilizing the speed-vac, and dissolved in DMSO for biological testing.

Example 9

General Method for Synthesis of Piperzinones According to Method A

The $N^\alpha$-Fmoc- amino acid derivitized resin is treated with DMF in a silanized (Sigmacote) reaction vessel, and agitated for 30 minutes. The DMF is filtered away and the resin is treated with 25% piperidine in DMF (~20 mL/g resin). The deprotection reaction is agitated with nitrogen for 25 minutes. The solvent is then filtered away, and the resin reacted again for 25 minutes with 25% piperidine in DMF with nitrogen bubbling. The reaction mixture is filtered away and the resin is washed well with DMF, dichloromethane, methanol, and dichloromethane. The resin can then be stored under nitrogen at low temperature. Dried resin is suspended in DMF and agitated for 30 minutes; the DMF is filtered away and the resin is then treated with DMF (~40 mL/mmole) containing 1% acetic acid. Three equivalents of the appropriate aldehyde is added followed by 10 equivalents of sodium cyanoborohydride. The reaction is agitated by nitrogen bubbling for 6 to 24 hours. Reaction progress can be assessed by the Kaiser test or by HPLC analysis of a TFA cleavage reaction of a few resin beads. If incomplete reaction is obtained, the reaction is filtered and resubmitted to the reductive amination conditions. When complete reductive amination is achieved the reaction mixture is filtered and washed well with DMF then dichloromethane, followed by another series of DMF washes. The resin immobilized N-substituted amino acid is then bromoacetylated with a solution of 12 equivalents of bromoacetic acid and 13.2 equivalents of diisopropyl-carbodiimide in DMF (~10 mL/g resin). The reaction is agitated for 30 minutes, filtered, washed with DMF, and treated a second time with 12 equivalents of bromoacetic acid and 13.2 equivalents of diisopropyl-carbodiimide in DMF (~10 mL/g resin). After 30 minutes of nitrogen agitation the solution is filtered, washed well with DMF, dichloromethane and dried under a nitrogen stream. The resin is then dried under vacuum. The resin is treated with a solution of an appropriate primary amine (0.25 to 2M) in DMSO (~1 mL/100 mg of resin). The reaction may be sonicated for 3 hours or agitated for approximately 15 hours. The mixture is then filtered, washed well with DMF, dichloromethane, methanol, and finally with dichloromethane. The derivatized resin is then dried in a stream of nitrogen and then under vacuum if storage is necessary. The dried resin or slurried aliquots are transferred to a round bottom flask or mini-reactor tube and treated with 2-butanol containing 11% (v/v) acetic acid (~5 to 10 mL/mg resin). The reaction vessel is placed in a 110° oil bath and heated at reflux under nitrogen for 48 to 72 hours. The crude piperazinedione is isolated by filtration, and washing of the resin with acetonitrile, methanol, and dichloromethane. The volatile solvents are removed by rotary evaporation. The product may be purified by HPLC chromatography. Side chain protecting groups such as Cbz and Boc are conviently deprotected at this stage, before $LiAlH_4$ reduction. Free amino groups formed by deprotection may be acylated or guanidated.

Example 10

General Method for Combinatorial Synthesis of Mixtures of Piperzinones According to Method A A large combinatorial library of piperazines and piperazinediones was synthesized as follows.

A. Resin Mixing, Deprotection and Slurry Splitting

The following $N^\alpha$-Fmoc amino acid resins were mixed in a large silanized solid phase peptide synthesis apparatus.

| Fmoc-Amino Acid | Loading (meq/g) | mMoles | Amount used. |
|---|---|---|---|
| L-Phenylalanine | 0.72 | 0.625 | 0.87 g |
| D-Phenylalanine | 0.81 | 0.625 | 0.77 g |
| L-Tryptophan | 0.66 | 0.625 | 0.95 g |
| D-Tryptophan | 0.57 | 0.625 | 1.10 g |
| D,L-Cha | 0.57 | 1.25 | 2.20 g |
| D,L-2-Nal | 0.55 | 1.25 | 2.28 g |
| D,L-Igl | 0.50 | 1.25 | 2.50 g |
| 10 (5 D,L Pairs) Total | 0.625 Average | 6.25 Total | 10.67 g total |

The resins were suspended in DMF and agitated for 30 minutes, the DMF was filtered away and treated with 200 mL of 25% piperidine in DMF with nitrogen agitation for 25 minutes. The solution was drained away and the resin was again treated with 200 mL of 25% piperidine in DMF with nitrogen agitation for 25 minutes. The solution was filtered away and the resin was washed well with DMF and dichloromethane. The resin was slurried in a mixture of 3:2 dichloroethane:dimethylformamide (V/V), and the the slurry was volumetrically divided into 12 equal portions which were filtered, washed with dimethylformamide and dichloromethane and dried under vacuum. These 12 resin lots were given letter designations A through L for simplification for experimental description.

B: Reductive Amination

Each resin lot was reacted with the appropriate aldehyde or ketone as follows.

| A | cyclohexanone |
|---|---|
| B | cyclohexane carboxaldehyde |
| C | benzaldehyde |
| D | phenylacetaldehyde |
| E | 4'-biphenylcarboxaldehyde |
| F | No reductive amination. |
| G | 2-Napthaldehyde |
| H | 2-indanone |
| I | 2-(N-Cbz)-ethanal |
| J | 6-(N-Cbz)-hexanal |
| K | 12-(N-Cbz)-dodecanal |

Each resin lot was placed in a 50 mL solid phase reaction vessel, suspended in dimethylformamide (20 mL) and agitated for 30 minutes. The solvent was drained away and the resin was treated with 25 to 30 mL of dimethylformamide containing 3 equivalents (1.56 mmole) of aldehyde or ketone and 10 equivalents (327 mg) of sodiumcyanoborohydride. The reaction was agitated for 6 to 24 hours, and monitored by the Kaiser test. If incomplete reaction had occured the mixture was filtered away and a fresh solution of 25 to 30 mL of dimethylformamide containing 3 equivalents (1.56 mmole) of aldehyde or ketone and 10 equivalents (327 mg) of sodiumcyanoborohydride was added and reaction was continued for 6 to 24 hours. The reaction mixture was then filtered away and the resin mixtures were washed well with dimethylformamide and dichloromethane and dried under vacuum.

C. Bromoacetylation

All lots A through L were bromoacetylated as follows. Each resin sample was placed in a 50 mL solid phase synthesis reaction vessel and suspended in DMF. The mixture was agitated for 30 minutes, and filtered away. The resin was then reacted with 12 equivalents bromoacetic acid (867 mg) and 13.2 equivalents of diisopropylcarbodiimide (1.08 mL) in DMF (~10 mL/g resin). The reaction was agitated for 60 minutes, after which the solution was filtered away. The reaction vessel was charged with fresh bromoacetylation cocktail and the reaction was again agitated for 60 minutes. The solution was drained away and each lot was washed well with dimethylformamide followed by dichloromethane and dried under vacuum.

D. Amine Displacement Reactions

Amines #1 through #12 used in displacement reactions:

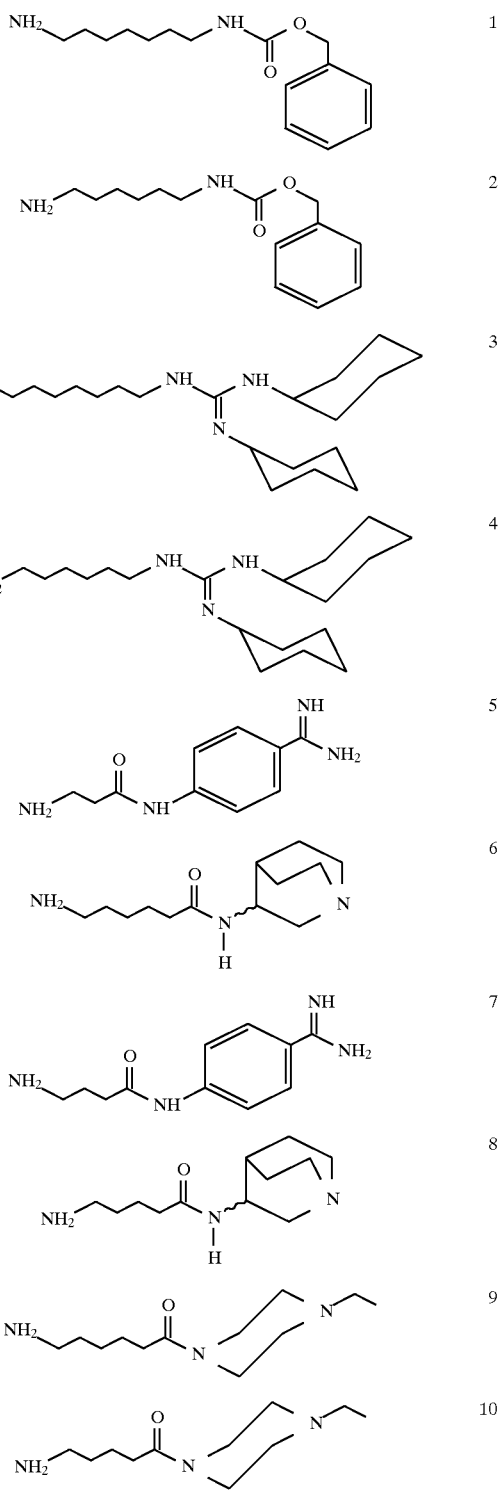

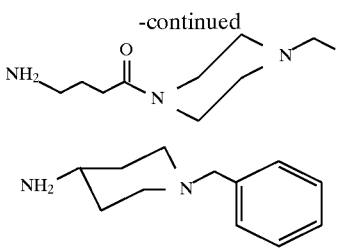

D. Amine Displacement Reactions

Each lettered lot of Resin (A through L) following bromoacetylation was again subdivided into 12 sub-lots and numbered sequentially i.e. (A1 through A12, B1 through B12, . . . L1 through L12). Each sublot was reacted with the corresponding numbered amine as follows.

| Amine # | Equivalents | Concentration in DMSO |
|---|---|---|
| 1 | 20 | 0.43 M |
| 2 | 20 | 0.43 M |
| 3 | 9 | 0.193 M |
| 4 | 13 | 0.284 M |
| 5 | 14.5 | 0.315 M |
| 6 | 14 | 0.302 M |
| 7 | 20 | 0.43 M |
| 8 | 23 | 0.50 M |
| 9 | 23 | 0.50 M |
| 10 | 23 | 0.50 M |
| 11 | 17.5 | 0.38 M |
| 12 | 20 | 0.43 M |

Reactions were carried out in a specially designed multiple reaction device which is described in example 438. The 5 ml reaction vessles were pre-loaded with the appropriate amine solution in DMSO. Hydrochloride salts were treated with 2 equivalents of diisopropylethylamine in situ to provide free amino groups for the displacement reaction. The reactions were allowed to swirl for 15 hours or were sonicated at approximately 50° C. for 3 hours. The reaction flasks were then removed and the resin samples were washed by positive $N_2$ pressure using DMSO, DMF, dichloromethane, methanol, and dichloromethane.

E. Cyclization Reactions

A fresh set of 12 5 mL reaction vessels charged with 3 mL of 2-butanol containing 2M acetic acid are connected to the multiple reaction device so each resin sample is immersed in solution. The exposed gas dispersion tubes are connected to positive pressure nitrogen lines and cooled externally with dry ice. The 5 mL reaction vessels are placed in a 110° C. oil bath and heated for 48 to 90 hours. From time to time fresh butanol containing 2M acetic acid is added to maintain approximately 3 mL volume. After the reflux period the reaction flasks containing the now cleaved and cyclized piperzazine-diones are removed and the solvent removed by rotary evaporation. Completed piperazinedione mixtures are assayed by HPLC and laser desorption mass spectrometry, dissolved in a predetermined volume of DMSO and assayed for receptor binding or enzyme inhibition activity.

F. Further Reactions

Piperazinedione mixtures derived from amines #1 and #2 are deprotected with hydrogen bromide in acetic acid as described in example 4, and can be acylated or guanidinated as described above or tested as free amines. All sublots were divided in half and reduced with lithium aluminum hydride as described in example 11.

Example 11

General Procedure for $LiAlH_4$ Reduction of Mixtures of Piperazinediones from Example 10

The piperazinediones obtained from cyclization reactions or following protecting group removal, as residues in 5 mL flasks, are carefully treated with 1M $LiAlH_4$ solution (20 equivalents) and attached to the multiple reaction device. In these instances, a plain glass column replaces the gas dispersion tube and positive nitrogen pressure is provided by plastic tubing attached to the glass column. External cooling of the condensor tubing is provided by packing the exposed glass and plastic tubing in dry ice. The 5 mL flasks are then placed in an 80° C. oil bath and the reactions refluxed 16 hours. The reactions are cooled to room temperature and poured into ice. The flasks are rinsed well sequentially with dichloromethane, methanol and water. The volatile organic solvents and water are removed on a speed-vac and the residue is extracted with acetonitrile (1.5 mL), evaporated and assayed or submitted to further modification such as acylation or guanidination.

Example 12

Bradykinin 2 Guinea Pig Ileum Receptor Binding Assay

Guinea pig ileum membranes were preparation by Analytical Biological Services, Inc. Briefly, ilea were finely chopped and combined with TES buffer (25 mM, pH 6.8) containing 1 mM 1, 10-phenanthroline, 5 ug/ml soybean trypsin inhibitor, 100 ug/ml bacitracin, 1 mM benzamidine, and 100 uM phenylmethylsulfonyl fluoride. This mixture was homogenized in a Brinkman PT-20 Polytron (setting 7,4×20 sec intervals) and subjected to differential centrifugation (1000× g, 4° C., 10 min). The pellet was discarded and the supernatant centrifuged for 15 min at 43,000× g at 4° C. The pellet was washed twice by resuspending in the buffer described above and centrifuging as above. The pellet was resuspended and stored at −70° C. until use.

Guinea pig ileum membrane solution were incubated with $^3$H-bradykinin (final concentration 0.3 nM) with or without test compounds in assay buffer (25 mM TES, pH 6.8 containing 1 mM 1,10 phenanthroline, 1 mM dithiothreitol, 2 uM captopril, 140 ug/ml bacitracin, and 0.1% bovine serum albumin, BSA), at room temperature, for 45 minutes, at a final volume of 315 ul. All test compound dilutions were done in triplicate. Assays were harvested by quick filtration in a Tomtec Harvester 96, with ice-cold wash buffer consisting of 10 mM Tris/HCl, pH 7.5, 100 mM NaCl,0.02% BSA, onto Wallec printed glassfiber Filtermat "B", which had been pre-soaked with 0.1% polyethyleneimine (PEI) and previously air-dried. Filtermats were counted in 9.5 ml Wallec Beta-Plate Scint, in Wallec 1450 MicroBeta Counter.

Example 13

Bradykinin 2 and Bradykinin 1 Human Receptor Clone Binding Assays

Human bradykinin $B_2$ receptor was expressed in CHO-K1 (ATCC) cells. Preparation of membranes for binding assay was carried out by scraping cells from roller bottles in ice cold PBS and centrifuging at 1000× g, at 4° C. for 15 minutes. The supernatant was discarded and pellet resuspended in Buffer A consisting of 25 mM TES (pH 6.8) with 2 uM 1,10-phenanthroline, and centrifuged at 27,000× g for 15 min. The pellet was washed once using the same buffer and centrifugation parameters. The final pellet was resuspended in Buffer B (Buffer A with 2 uM captopril, 140 ug/ml bacitracin, 0.1% BSA), and stored in 1 ml aliquot, frozen at −70° C. until needed.

$B_2$ Binding assays were performed by incubating human clone membrane solution with $^3$H-bradykinin (final concentration 0.3 nM) with or without test compounds in assay buffer (Buffer B with 1 mM dithiothreitol), at room temperature, for 45 minutes, at a final volume of 315 ul. All test compound dilutions were done in triplicate. Assays were harvested by quick filtration in a Tomtec Harvester 96, with ice-cold wash buffer consisting of 10 mM Tris/HCl, pH 7.5, 100 mM NaCl,0.02% BSA, onto Wallec printed glassfiber Filtermat "B", which had been pre-soaked with 0.1% PEI and previously air-dried. Filtermats were counted in 9.5 ml Wallec Beta-Plate Scint, in Wallec 1450 MicroBeta Counter.

Human lung fibroblasts IMR-90 cells were obtained from ATCC and propagated in DMEM media in 850 mm roller bottles until confluent. Three hours prior to harvesting, the cells were treated with interleukin 1-beta (200 pg/ml). After three hours, cells were scraped from roller bottles in ice cold PBS and centrifuging at 1000× g, at 4° C. for 15 minutes. The supernatant was discarded and pellet resuspended in Buffer A consisting of 25 mM TES (pH 6.8) with 2 uM 1,10-phenanthroline, and centrifuged at 27,000× g for 15 min. The pellet was washed once using the same buffer and centrifugation parameters. The final pellet was resuspended in Buffer B (Buffer A with 2 uM captopril, 140 ug/ml bacitracin, 0.1% BSA), and stored in 1 ml aliquot, frozen at −70° C. until use.

The human bradykinin B1 binding assays were performed by incubating IMR-90 membrane solution (approx. 150 ug/well) with $^3$H-des-Arg$^{10}$Kallidin, (final concentration 0.5 nM) with or without test compounds in assay buffer (Buffer B with 1 mM dithiothreitol), at room temperature, for 45 minutes, at a final volume of 200 ul. All test compound dilutions were done in triplicate. Assays were harvested by quick filtration in a Tomtec Harvester 96, with ice-cold wash buffer consisting of 10 mM Tris/HCl, pH 7.5, 100 mM NaCl, 0.02% BSA, onto Wallec printed glassfiber Filtermat "B", which had been pre-soaked with 0.1% PEI and previously air-dried. Filtermats were counted in 9.5 ml Wallac Beta-Plate Scint, in Wallace 1450 MicroBeta Counter.

Example 14

Neurokinin 1 Human Receptor Clone Binding Assay

The human NK-1 receptor was expressed in CHO-K1 (ATCC) cells. Preparation of membranes for binding assay was carried out by scraping cells from culture flasks in ice cold PBS and centrifuging at 500× g, at 4° C. for 10 minutes. The supernatant was discarded and pellet resuspended in 50 mM Tris/HCl, pH 7.4 with 1 mM 1,10 phenanthroline, and centrifuged at 27,000× g for 15 min. The pellet was washed once using 20 mM HEPES, pH 7.4,5 mM MgCl$_2$, 30 mM KCl, 0.02% BSA and 100 uM thiorphan and centrifuged as above. The final pellet was resuspended in the wash buffer (above) and stored in 1 ml aliquot, frozen at −70° C. until needed.

Human NK1 receptor binding assays were performed by incubating human clone membrane solution (50 ug/well in 125 ul) with $^3$H-substance P (final concentration 1.0 nM) with or without test compounds in assay buffer (Buffer B with 1 mM dithiothreitol), at room temperature, for 30 minutes, at a final volume of 315 ul. All test compound dilutions were done in triplicate. Assays were harvested by quick filtration in a Tomtec Harvester 96, with ice-cold wash buffer consisting of 20 mM Tris/HCl, pH 7.5, 120 mM NaCl, 5 mM KCl and 0.02% BSA, onto Wallec printed glassfiber Filtermat "B", which had been pre-soaked with 0.1% PEI and previously air-dried. Filtermats were counted in 9.5 ml Wallec Beta-Plate Scint, in Wallec 1450 MicroBeta Counter.

Example 15

Neurokinin 2 Human Receptor Clone Binding Assay

The cell membrane preparation and receptor binding procedure are identical to that described above for the NK-1 receptor (Example 14) except that $^3$H-neurokinin A was used as the ligand at 2.0 nM.

Example 16

Mu-Opioid Human Receptor Clone Binding Assay

The human mu-opioid receptor was expressed in CHO-K1 (ATCC) cells. Preparation of membranes for binding assay was carried out by scraping cells from culture flasks in ice cold PBS and centrifuging at 500× g, at 4° C. for 10 minutes. The supernatant was discarded and pellet resuspended in 10 mM Tris/HCl, pH 7.4 with 0.32M sucrose and centrifuged for 30 min at 40C at 27,000× g. The supernatant was discarded and the pellet resuspended in the wash buffer (above) and stored in 1 ml aliquot, frozen at −70° C. until needed.

Human mu-opioid binding assays were performed by incubating human clone membrane solution (50 ug/well in 125 ul) with $^3$H-DAMGO ([D-Ala$^2$, N-Me-Phe$^4$, Gly$^5$-ol] enkephalin; final concentration 5.0 nM) with or without test compounds in assay buffer (Buffer B with 1 mM dithiothreitol), at room temperature, for 60 minutes, at a final volume of 315 ul. All test compound dilutions were done in triplicate. Assays were harvested by quick filtration in a Tomtec Harvester 96, with ice-cold wash buffer consisting of 50 mM Tris/HCl, pH 7.4 onto Wallec printed glassfiber Filtermat "B", which had been pre-soaked with 0.1% PEI and previously air-dried. Filtermats were counted in 9.5 ml Wallec Beta-Plate Scint, in Wallec 450 MicroBeta Counter.

Example 17 k-Opioid Guinea Pig Brain Receptor Binding Assay

Preparation of guinea pig brain membrane for Kappa binding assay was carried out by homogenizing tissue with 5 second bursts of tissue homogenizer, until smooth, in ice-cold assay buffer consisting of 10 mM Tris/HCl, pH 7.4 with 0.32M Sucrose. The homogenate was centrifuged at 1,500× g, for 10 minutes at 4° C. The pellet was discarded and supernatant was centrifuged at 30,000× g, for 30 min at 4° C. Supernatant was discarded and pellet resuspended in fresh assay buffer, and in 1 ml aliquot, frozen at −70° C. until needed. Protein concentration was determined by Bradford analysis.

k-Opioid receptro binding assays were performed by incubating guinea pig brain membrane solution (50 ug/well in 125 ul final concentration) with $^3$H-U69,593 (final concentration 5.0 nM, New England Nuclear) with or without test compounds in assay buffer, at room temperature, for 60 minutes, at a final volume of 315 ul. All test compound dilutions were done in triplicate. To block mu receptor sites, 0.1 uM solution of unlabeled DAMGO, in assay buffer, was added to all wells. Assays were harvested by quick filtration in a Tomtec Harvester 96, with ice-cold wash buffer consisting of 50 mM Tris/HCl, pH 7.4, onto Wallec printed glassfiber Filtermat "B", which had been pre-soaked with 0.1% PEI and previously air-dried. Filtermats were counted in 9.5 ml Wallec Beta-Plate Scint, in Wallec 1450 MicroBeta Counter.

Example 18

Bradykinin Induced Calcium Flux in Human WI38 Fibroblasts

A fluorescent indicator (Fura-2) method was used to measure cytosolic Ca(+2) (A. Pilyavskaya et al. FASEB J. 9, 6, A1371, 1995). Human lung fibroblasts are loaded with Fura-2 and, after incubation with BK in the absence and presence of antagonists, the cells are analyzed in a Perkin-Elmer LS50B spectrofluorometer using excitation wavelengths of 340 & 380 nm and an emission wavelength of 510 nm. Cells are maintained in suspension during the measurements.

Examples 19–39. Specific Piperazines and Piperazinediones Prepared According to Method B.

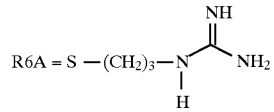
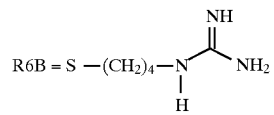
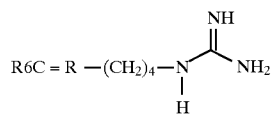
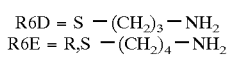
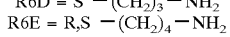
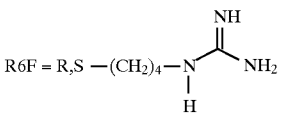

| Example | X | $R^5$ | $R^7$ | $R^6$ | HPLC[a] | Mass Spec. (M + H) | CP |
|---|---|---|---|---|---|---|---|
| 19 | O | R-benzyl | —CH$_2$—C$_6$H$_{11}$ | R6A | 20.0 | 400 | 2006 |
| 20 | H$_2$ | R-benzyl | —CH$_2$—C$_6$H$_{11}$ | R6D | 17.8 | 343 | 2011 |
| 21 | H$_2$ | R-benzyl | —CH$_2$—C$_6$H$_{11}$ | R6A | 19.6 | 386 | 2012 |
| 22 | H$_2$ | R-benzyl | —C$_6$H$_{11}$ | R6B | 17.3 | 372 | 2029 |
| 23 | H$_2$ | R-benzyl | benzyl | R6B | 18.1 | 380 | 2034 |
| 24 | H$_2$ | R-benzyl | 2-indanyl | R6B | 21.2 | 406 | 2035 |
| 25 | H$_2$ | S-benzyl | —C$_6$H$_{11}$ | R6B | 16.5 | 372 | 2051 |
| 26 | H$_2$ | S-benzyl | —CH$_2$—C$_6$H$_{11}$ | R6B | 19.7 | 386 | 2052 |
| 27 | H$_2$ | S-benzyl | benzyl | R6B | 19.5 | 380 | 2053 |
| 28 | H$_2$ | S-benzyl | —CH$_2$CH$_2$Ph | R6B | 19.5 | 393 | 2054 |
| 29 | H$_2$ | S-benzyl | —C$_6$H$_{11}$ | R6C | 17.0 | 372 | 2075 |
| 30 | H$_2$ | S-benzyl | —CH$_2$—C$_6$H$_{11}$ | R6C | 17.3 | 386 | 2076 |
| 31 | H$_2$ | S-benzyl | benzyl | R6C | 17.8 | 380 | 2077 |
| 32 | H$_2$ | S-benzyl | —CH$_2$CH$_2$Ph | R6C | 19.1 | 393 | 2078 |
| 33 | H$_2$ | R-benzyl | —CH$_2$CH$_2$Ph | R6B | 18.3 | 394 | 2080 |
| 34 | H$_2$ | R-benzyl | —CH$_2$—C$_6$H$_{11}$ | R6B | 18.7 | 386 | 2081 |
| 35 | H$_2$ | R-benzyl | CH$_2$—C$_6$H$_{11}$ | R6C | 17.6 | 386 | 2082 |
| 36 | H$_2$ | R-benzyl | —CH$_2$CH$_2$Ph | R6C | 18.0 | 394 | 2083 |
| 37 | H$_2$ | R,S-2-indanyl | 3,4 Di-MeOBn | R6E | 17–18 | 425 | 2102 |
| 38 | H$_2$ | R,S-2-indanyl | —CH$_2$—C$_6$H$_{11}$ | R6F | 20.3/22.1 | 412 | 2103 |
| 39 | H$_2$ | R,S,-benzyl | 3,4 Di-MeOBn | R6F | 17.4/18.0 | 440 | 2104 |

Examples 40–61. Specific Piperazines and Piperazinediones Prepared According to Method A.

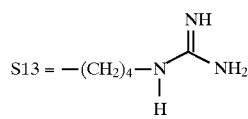
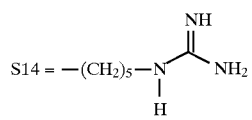
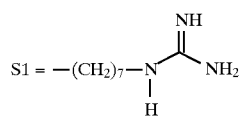

-continued

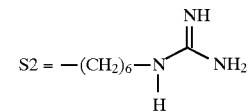

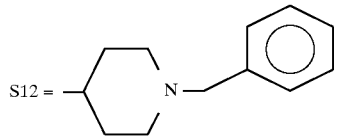

| CP# | Example | X | R1 | R2 | R3 | HPLC | MS (M + H) |
|---|---|---|---|---|---|---|---|
| 2114 | 40 | H2 | R,S-benzyl | —CH$_2$—C$_6$H$_{11}$ | S13 | 19.9 | 386 |
| 2115 | 41 | H2 | R,S-benzyl | —CH$_2$—C$_6$H$_{11}$ | S14 | 19.8 | 400 |
| 2116 | 42 | H2 | R,S-benzyl | —CH$_2$—C$_6$H$_{11}$ | S2 | 19.5 | 414 |
| 2117 | 43 | H2 | R,S-benzyl | —CH$_2$—C$_6$H$_{11}$ | S1 | 20.2 | 428 |
| 2151 | 44 | O | S-benzyl | H | S1 | 16.7 | 360 |
| 2371 | 45 | O | S-3-indole | —CH$_2$CH$_2$Ph | S12 | 24.1 | 521 |
| 2372 | 46 | O | R-3-indole | —CH$_2$CH$_2$Ph | S12 | 24.1 | 521 |
| 2373 | 47 | O | S-benzyl | —CH$_2$CH$_2$Ph | S12 | 24.0 | 482 |
| 2374 | 48 | O | R-benzyl | —CH$_2$CH$_2$Ph | S12 | 24.0 | 482 |
| 2399 | 49 | O | S —CH$_2$—C$_6$H$_{11}$ | —CH$_2$CH$_2$Ph | S12 | 29.0 | 488 |
| 2400 | 50 | O | R —CH$_2$—C$_6$H$_{11}$ | —CH$_2$CH$_2$Ph | S12 | 29.0 | 488 |
| 2425 | 51 | O | S —CH$_2$-2-Nph | —CH$_2$CH$_2$Ph | S12 | 27.3 | 532 |
| 2426 | 52 | O | R —CH$_2$-2-Nph | —CH$_2$CH$_2$Ph | S12 | 27.5 | 532 |
| 2427 | 53 | O | H | —CH$_2$CH$_2$Ph | S12 | 18.4 | 392 |
| 2428 | 54 | O | R,S-2-indanyl | —CH$_2$CH$_2$Ph | S12 | 26.5 | 508 |
| 2429 | 55 | O | S —CH$_2$-2-Nph | —CH$_2$C$_6$H$_{11}$ | S12 | 29.1 | 524 |
| 2430 | 56 | O | R —CH$_2$-2-Nph | —CH$_2$C$_6$H$_{11}$ | S12 | 29.2 | 524 |
| 2431 | 57 | O | R,S-2-indanyl | —CH$_2$C$_6$H$_{11}$ | S12 | 29.1 | 500 |
| 2456 | 58 | O | S —CH$_2$—C$_6$H$_{11}$ | CH$_2$C$_6$H$_{11}$ | S12 | 31.2 | 480 |
| 2457 | 59 | O | R —CH$_2$—C$_6$H$_{11}$ | CH$_2$C$_6$H$_{11}$ | S12 | 31.3 | 480 |
| 2458 | 60 | O | R,S-2-indanyl | CH$_2$-2-Nph | S2 | 28.1 | 512 |
| 2459 | 61 | O | R,S-2-indanyl | 4'-biphenyl | S1 | 31.0 | 552 |

Examples 62 through 437. Combinatorial Mixtures of Piperazindiones and Piperazines Prepared According to Methods 4, 6, 10, 11.

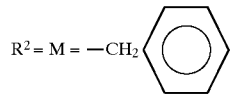

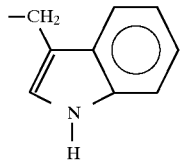

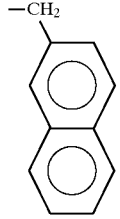

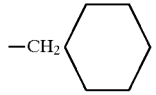

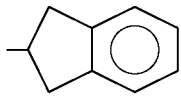

-continued
A = 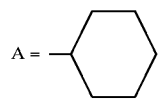
B = 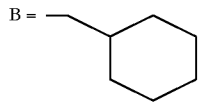
C = 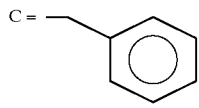
D = 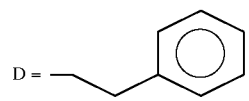
E = 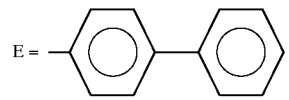
F1 = 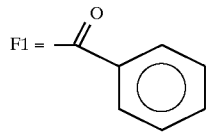
F2 = H
G = 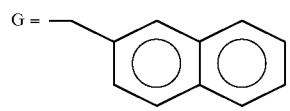
H = 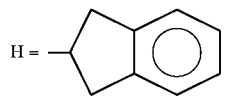
I = 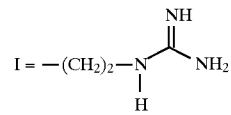
$I_{NH2}$ = —$(CH_2)_2$—$NH_2$
$I_{Cbz}$ = —$(CH_2)_2$—NHCbz
J = 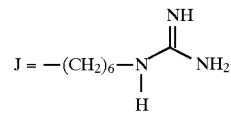
$J_{NH2}$ = —$(CH_2)_6$—$NH_2$
$J_{Cbz}$ = —$(CH_2)_6$—NHCbz
K = 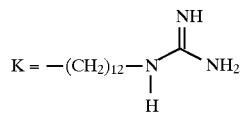
$K_{NH2}$ = —$(CH_2)_{12}$—$NH_2$
$K_{Cbz}$ = —$(CH_2)_{12}$—NHCbz
L = 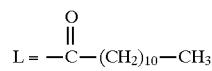

-continued
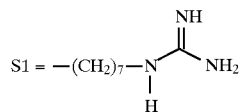
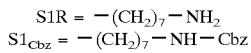
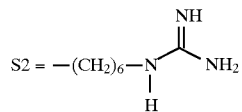
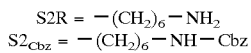
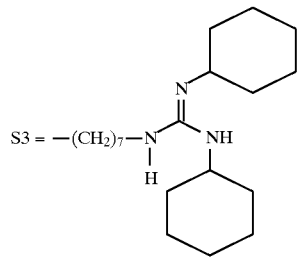
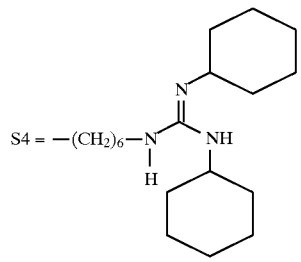
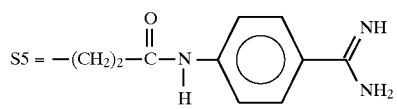
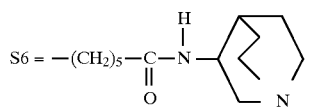
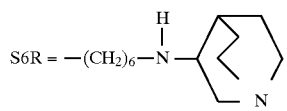
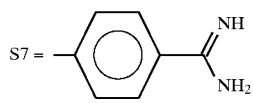
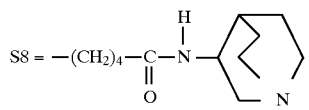
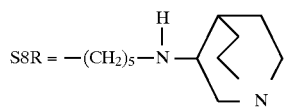

-continued
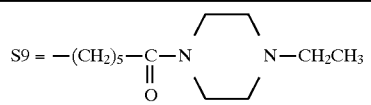
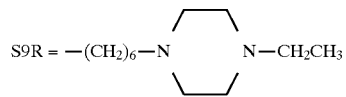
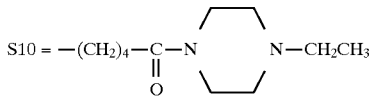
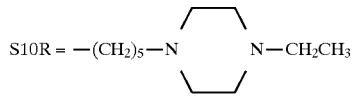
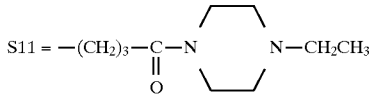
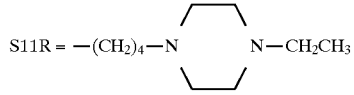
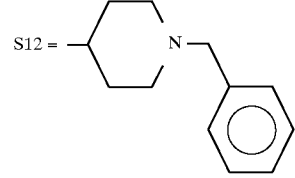
| Example | X | R1 | R2 | R3 |
| --- | --- | --- | --- | --- |
| 62 | O | A | M | S1 |
| 63 | O | A | M | S2 |
| 64 | O | A | M | S1R |
| 65 | O | A | M | S2R |
| 66 | O | A | M | S3 |
| 67 | O | A | M | S4 |
| 68 | O | A | M | S5 |
| 69 | O | A | M | S6 |
| 70 | O | A | M | S7 |
| 71 | O | A | M | S8 |
| 72 | O | A | M | S9 |
| 73 | O | A | M | S10 |
| 74 | O | A | M | S11 |
| 75 | O | A | M | S12 |
| 76 | O | A | M | S1Cbz |
| 77 | O | A | M | S2Cbz |
| 78 | $H_2$ | A | M | S1R |
| 79 | $H_2$ | A | M | S2R |
| 80 | $H_2$ | A | M | S6R |
| 81 | $H_2$ | A | M | S8R |
| 82 | $H_2$ | A | M | S9R |
| 83 | $H_2$ | A | M | S10R |
| 84 | $H_2$ | A | M | S11R |
| 85 | $H_2$ | A | M | S12 |
| 86 | $H_2$ | A | M | S1 |
| 87 | $H_2$ | A | M | S2 |
| 88 | O | B | M | S1 |
| 89 | O | B | M | S2 |
| 90 | O | B | M | S1R |
| 91 | O | B | M | S2R |
| 92 | O | B | M | S3 |
| 93 | O | B | M | S4 |
| 94 | O | B | M | S5 |
| 95 | O | B | M | S6 |
| 96 | O | B | M | S7 |
| 97 | O | B | M | S8 |

-continued

| | | | | |
|---|---|---|---|---|
| 98 | O | B | M | S9 |
| 99 | O | B | M | S10 |
| 100 | O | B | M | S11 |
| 101 | O | B | M | S12 |
| 102 | O | B | M | S1Cbz |
| 103 | O | B | M | S2Cbz |
| 104 | $H_2$ | B | M | S1R |
| 105 | $H_2$ | B | M | S2R |
| 106 | $H_2$ | B | M | S6R |
| 107 | $H_2$ | B | M | S8R |
| 108 | $H_2$ | B | M | S9R |
| 109 | $H_2$ | B | M | S10R |
| 110 | $H_2$ | B | M | S11R |
| 111 | $H_2$ | B | M | S12 |
| 112 | $H_2$ | B | M | S1 |
| 113 | $H_2$ | B | M | S2 |
| 114 | O | C | M | S1 |
| 115 | O | C | M | S2 |
| 116 | O | C | M | S1R |
| 117 | O | C | M | S2R |
| 118 | O | C | M | S3 |
| 119 | O | C | M | S4 |
| 120 | O | C | M | S5 |
| 121 | O | C | M | S6 |
| 122 | O | C | M | S7 |
| 123 | O | C | M | S8 |
| 124 | O | C | M | S9 |
| 125 | O | C | M | S10 |
| 126 | O | C | M | S11 |
| 127 | O | C | M | S12 |
| 128 | O | C | M | S1Cbz |
| 129 | O | C | M | S2Cbz |
| 130 | $H_2$ | C | M | S1R |
| 131 | $H_2$ | C | M | S2R |
| 132 | $H_2$ | C | M | S6R |
| 133 | $H_2$ | C | M | S8R |
| 134 | $H_2$ | C | M | S9R |
| 135 | $H_2$ | C | M | S10R |
| 136 | $H_2$ | C | M | S11R |
| 137 | $H_2$ | C | M | S12 |
| 138 | $H_2$ | C | M | S1 |
| 139 | $H_2$ | C | M | S2 |
| 140 | O | D | M | S1 |
| 141 | O | D | M | S2 |
| 142 | O | D | M | S1R |
| 143 | O | D | M | S2R |
| 144 | O | D | M | S3 |
| 145 | O | D | M | S4 |
| 146 | O | D | M | S5 |
| 147 | O | D | M | S6 |
| 148 | O | D | M | S7 |
| 149 | O | D | M | S8 |
| 150 | O | D | M | S9 |
| 151 | O | D | M | S10 |
| 152 | O | D | M | S11 |
| 153 | O | D | M | S12 |
| 154 | O | D | M | S1Cbz |
| 155 | O | D | M | S2Cbz |
| 156 | $H_2$ | D | M | S1R |
| 157 | $H_2$ | D | M | S2R |
| 158 | $H_2$ | D | M | S6R |
| 159 | $H_2$ | D | M | S8R |
| 160 | $H_2$ | D | M | S9R |
| 161 | $H_2$ | D | M | S10R |
| 162 | $H_2$ | D | M | S11R |
| 163 | $H_2$ | D | M | S12 |
| 164 | $H_2$ | D | M | S1 |
| 165 | $H_2$ | D | M | S2 |
| 166 | O | E | M | S1 |
| 167 | O | E | M | S2 |
| 168 | O | E | M | S1R |
| 169 | O | E | M | S2R |
| 170 | O | E | M | S3 |
| 171 | O | E | M | S4 |
| 172 | O | E | M | S5 |
| 173 | O | E | M | S6 |
| 174 | O | E | M | S7 |
| 175 | O | E | M | S8 |
| 176 | O | E | M | S9 |
| 177 | O | E | M | S10 |

| | | | | |
|---|---|---|---|---|
| 178 | O | E | M | S11 |
| 179 | O | E | M | S12 |
| 180 | O | E | M | S1Cbz |
| 181 | O | E | M | S2Cbz |
| 182 | H$_2$ | E | M | S1R |
| 183 | H$_2$ | E | M | S2R |
| 184 | H$_2$ | E | M | S6R |
| 185 | H$_2$ | E | M | S8R |
| 186 | H$_2$ | E | M | S9R |
| 187 | H$_2$ | E | M | S10R |
| 188 | H$_2$ | E | M | S11R |
| 189 | H$_2$ | E | M | S12 |
| 190 | H$_2$ | E | M | S1 |
| 191 | H$_2$ | E | M | S2 |
| 192 | O | F2 | M | S1 |
| 193 | O | F2 | M | S2 |
| 194 | O | F2 | M | S1R |
| 195 | O | F2 | M | S2R |
| 196 | O | F2 | M | S3 |
| 197 | O | F2 | M | S4 |
| 198 | O | F2 | M | S5 |
| 199 | O | F2 | M | S6 |
| 200 | O | F2 | M | S7 |
| 201 | O | F2 | M | S8 |
| 202 | O | F2 | M | S9 |
| 203 | O | F2 | M | S10 |
| 204 | O | F2 | M | S11 |
| 205 | O | F2 | M | S12 |
| 206 | O | F2 | M | S1Cbz |
| 207 | O | F2 | M | S2Cbz |
| 208 | H$_2$ | F2 | M | S1R |
| 209 | H$_2$ | F2 | M | S2R |
| 210 | H$_2$ | F2 | M | S6R |
| 211 | H$_2$ | F2 | M | S8R |
| 212 | H$_2$ | F2 | M | S9R |
| 213 | H$_2$ | F2 | M | S10R |
| 214 | H$_2$ | F2 | M | S11R |
| 215 | H$_2$ | F2 | M | S12 |
| 216 | H$_2$ | F2 | M | S1 |
| 217 | H$_2$ | F2 | M | S2 |
| 218 | O | G | M | S1 |
| 219 | O | G | M | S2 |
| 220 | O | G | M | S1R |
| 221 | O | G | M | S2R |
| 222 | O | G | M | S3 |
| 223 | O | G | M | S4 |
| 224 | O | G | M | S5 |
| 225 | O | G | M | S6 |
| 226 | O | G | M | S7 |
| 227 | O | G | M | S8 |
| 228 | O | G | M | S9 |
| 229 | O | G | M | S10 |
| 230 | O | G | M | S11 |
| 231 | O | G | M | S12 |
| 232 | O | G | M | S1Cbz |
| 233 | O | G | M | S2Cbz |
| 234 | H$_2$ | G | M | S1R |
| 235 | H$_2$ | G | M | S2R |
| 236 | H$_2$ | G | M | S6R |
| 237 | H$_2$ | G | M | S8R |
| 238 | H$_2$ | G | M | S9R |
| 239 | H$_2$ | G | M | S10R |
| 240 | H$_2$ | G | M | S11R |
| 241 | H$_2$ | G | M | S12 |
| 242 | H$_2$ | G | M | S1 |
| 243 | H$_2$ | G | M | S2 |
| 244 | O | H | M | S1 |
| 245 | O | H | M | S2 |
| 246 | O | H | M | S1R |
| 247 | O | H | M | S2R |
| 248 | O | H | M | S3 |
| 249 | O | H | M | S4 |
| 250 | O | H | M | S5 |
| 251 | O | H | M | S6 |
| 252 | O | H | M | S7 |
| 253 | O | H | M | S8 |
| 254 | O | H | M | S9 |
| 255 | O | H | M | S10 |
| 256 | O | H | M | S11 |
| 257 | O | H | M | S12 |

-continued

| | | | | |
|---|---|---|---|---|
| 258 | O | H | M | S1Cbz |
| 259 | O | H | M | S2Cbz |
| 260 | H$_2$ | H | M | S1R |
| 261 | H$_2$ | H | M | S2R |
| 263 | H$_2$ | H | M | S6R |
| 264 | H$_2$ | H | M | S8R |
| 265 | H$_2$ | H | M | S9R |
| 266 | H$_2$ | H | M | S10R |
| 267 | H$_2$ | H | M | S11R |
| 268 | H$_2$ | H | M | S12 |
| 269 | H$_2$ | H | M | S1 |
| 270 | H$_2$ | H | M | S2 |
| 271 | O | I | M | S1 |
| 272 | O | I | M | S2 |
| 273 | O | I | M | S1R |
| 274 | O | I | M | S2R |
| 275 | O | I | M | S3 |
| 276 | O | I | M | S4 |
| 277 | O | I | M | S5 |
| 278 | O | I | M | S6 |
| 279 | O | I | M | S7 |
| 280 | O | I | M | S8 |
| 281 | O | I | M | S9 |
| 282 | O | I | M | S10 |
| 283 | O | I | M | S11 |
| 284 | O | I | M | S12 |
| 285 | O | I | M | S1Cbz |
| 286 | O | I | M | S2Cbz |
| 287 | H$_2$ | I | M | S1R |
| 288 | H$_2$ | I | M | S2R |
| 289 | H$_2$ | I | M | S6R |
| 290 | H$_2$ | I | M | S8R |
| 291 | H$_2$ | I | M | S9R |
| 292 | H$_2$ | I | M | S10R |
| 293 | H$_2$ | I | M | S11R |
| 294 | H$_2$ | I | M | S12 |
| 295 | H$_2$ | I | M | S1 |
| 296 | H$_2$ | I | M | S2 |
| 297 | O | J | M | S1 |
| 298 | O | J | M | S2 |
| 299 | O | J | M | S1R |
| 300 | O | J | M | S2R |
| 301 | O | J | M | S3 |
| 302 | O | J | M | S4 |
| 303 | O | J | M | S5 |
| 304 | O | J | M | S6 |
| 305 | O | J | M | S7 |
| 306 | O | J | M | S8 |
| 307 | O | J | M | S9 |
| 308 | O | J | M | S10 |
| 309 | O | J | M | S11 |
| 310 | O | J | M | S12 |
| 311 | O | J | M | S1Cbz |
| 312 | O | J | M | S2Cbz |
| 313 | H$_2$ | J | M | S1R |
| 314 | H$_2$ | J | M | S2R |
| 315 | H$_2$ | J | M | S6R |
| 316 | H$_2$ | J | M | S8R |
| 317 | H$_2$ | J | M | S9R |
| 318 | H$_2$ | J | M | S10R |
| 319 | H$_2$ | J | M | S11R |
| 320 | H$_2$ | J | M | S12 |
| 321 | H$_2$ | J | M | S1 |
| 322 | H$_2$ | J | M | S2 |
| 323 | O | K | M | S1 |
| 324 | O | K | M | S2 |
| 325 | O | K | M | S1R |
| 326 | O | K | M | S2R |
| 327 | O | K | M | S3 |
| 328 | O | K | M | S4 |
| 329 | O | K | M | S5 |
| 330 | O | K | M | S6 |
| 331 | O | K | M | S7 |
| 332 | O | K | M | S8 |
| 333 | O | K | M | S9 |
| 334 | O | K | M | S10 |
| 335 | O | K | M | S11 |
| 336 | O | K | M | S12 |
| 337 | O | K | M | S1Cbz |
| 338 | O | K | M | S2Cbz |

-continued

| | | | | |
|---|---|---|---|---|
| 339 | $H_2$ | K | M | S1R |
| 340 | $H_2$ | K | M | S2R |
| 341 | $H_2$ | K | M | S6R |
| 342 | $H_2$ | K | M | S8R |
| 343 | $H_2$ | K | M | S9R |
| 344 | $H_2$ | K | M | S10R |
| 345 | $H_2$ | K | M | S11R |
| 346 | $H_2$ | K | M | S12 |
| 347 | $H_2$ | K | M | S1 |
| 348 | $H_2$ | K | M | S2 |
| 349 | O | $K_{NH2}$ | M | S1R |
| 350 | O | $K_{NH2}$ | M | S2R |
| 351 | O | $K_{NH2}$ | M | S3 |
| 352 | O | $K_{NH2}$ | M | S4 |
| 353 | O | $K_{NH2}$ | M | S5 |
| 354 | O | $K_{NH2}$ | M | S6 |
| 355 | O | $K_{NH2}$ | M | S7 |
| 356 | O | $K_{NH2}$ | M | S8 |
| 357 | O | $K_{NH2}$ | M | S9 |
| 358 | O | $K_{NH2}$ | M | S10 |
| 359 | O | $K_{NH2}$ | M | S11 |
| 360 | O | $K_{NH2}$ | M | S12 |
| 361 | O | $K_{CBZ}$ | M | S3 |
| 362 | O | $K_{CBZ}$ | M | S4 |
| 363 | O | $K_{CBZ}$ | M | S5 |
| 364 | O | $K_{CBZ}$ | M | S6 |
| 365 | O | $K_{CBZ}$ | M | S7 |
| 366 | O | $K_{CBZ}$ | M | S8 |
| 367 | O | $K_{CBZ}$ | M | S9 |
| 368 | O | $K_{CBZ}$ | M | S10 |
| 369 | O | $K_{CBZ}$ | M | S11 |
| 370 | O | $K_{CBZ}$ | M | S12 |
| 371 | O | $K_{CBZ}$ | M | S1Cbz |
| 372 | O | $K_{CBZ}$ | M | S2Cbz |
| 373 | O | $I_{NH2}$ | M | S1R |
| 374 | O | $I_{NH2}$ | M | S2R |
| 375 | O | $I_{NH2}$ | M | S3 |
| 376 | O | $I_{NH2}$ | M | S4 |
| 377 | O | $I_{NH2}$ | M | S5 |
| 378 | O | $I_{NH2}$ | M | S6 |
| 379 | O | $I_{NH2}$ | M | S7 |
| 380 | O | $I_{NH2}$ | M | S8 |
| 381 | O | $I_{NH2}$ | M | S9 |
| 382 | O | $I_{NH2}$ | M | S10 |
| 384 | O | $I_{NH2}$ | M | S11 |
| 385 | O | $I_{NH2}$ | M | S12 |
| 386 | O | $I_{Cbz}$ | M | S3 |
| 387 | O | $I_{Cbz}$ | M | S4 |
| 388 | O | $I_{Cbz}$ | M | S5 |
| 389 | O | $I_{Cbz}$ | M | S6 |
| 390 | O | $I_{Cbz}$ | M | S7 |
| 391 | O | $I_{Cbz}$ | M | S8 |
| 392 | O | $I_{Cbz}$ | M | S9 |
| 393 | O | $I_{Cbz}$ | M | S10 |
| 394 | O | $I_{Cbz}$ | M | S11 |
| 395 | O | $I_{Cbz}$ | M | S12 |
| 396 | O | $I_{Cbz}$ | M | S1Cbz |
| 397 | O | $I_{Cbz}$ | M | S2Cbz |
| 398 | O | $J_{NH2}$ | M | S1R |
| 399 | O | $J_{NH2}$ | M | S2R |
| 400 | O | $J_{NH2}$ | M | S3 |
| 401 | O | $J_{NH2}$ | M | S4 |
| 402 | O | $J_{NH2}$ | M | S5 |
| 403 | O | $J_{NH2}$ | M | S6 |
| 404 | O | $J_{NH2}$ | M | S7 |
| 405 | O | $J_{NH2}$ | M | S8 |
| 406 | O | $J_{NH2}$ | M | S9 |
| 407 | O | $J_{NH2}$ | M | S10 |
| 408 | O | $J_{NH2}$ | M | S11 |
| 409 | O | $J_{NH2}$ | M | S12 |
| 410 | O | $J_{Cbz}$ | M | S3 |
| 411 | O | $J_{Cbz}$ | M | S4 |
| 412 | O | $J_{Cbz}$ | M | S5 |
| 413 | O | $J_{Cbz}$ | M | S6 |
| 414 | O | $J_{Cbz}$ | M | S7 |
| 415 | O | $J_{Cbz}$ | M | S8 |
| 416 | O | $J_{Cbz}$ | M | S9 |
| 417 | O | $J_{Cbz}$ | M | S10 |
| 418 | O | $J_{Cbz}$ | M | S11 |
| 419 | O | $J_{Cbz}$ | M | S12 |

-continued

| | | | | |
|---|---|---|---|---|
| 420 | O | J$_{Cbz}$ | M | S1Cbz |
| 421 | O | J$_{Cbz}$ | M | S2Cbz |
| 422 | H$_2$ | F1 | M | S6R |
| 423 | H$_2$ | F1 | M | S8R |
| 424 | H$_2$ | F1 | M | S9R |
| 425 | H$_2$ | F1 | M | S10R |
| 426 | H$_2$ | F1 | M | S11R |
| 427 | H$_2$ | F1 | M | S12 |
| 428 | H$_2$ | F1 | M | S1 |
| 429 | H$_2$ | F1 | M | S2 |
| 430 | H$_2$ | L | M | S6R |
| 431 | H$_2$ | L | M | S8R |
| 432 | H$_2$ | L | M | S9R |
| 433 | H$_2$ | L | M | S10R |
| 434 | H$_2$ | L | M | S11R |
| 435 | H$_2$ | L | M | S12 |
| 436 | H$_2$ | L | M | S1 |
| 437 | H$_2$ | L | M | S2 |

Example 438

Description of the Multiple Reaction Device

The multiple solid phase reaction device consists of polypropylene block clamps which may hold 1 to 12 or more mini-reactors. The mini-reactors consist of 5 mL round bottom flasks (Ace glass model 9592-04) with ground glass joints, and screw adapters, the resin is introduced into a gas dispersion tube ( 7 mm outside diameter, Ace glass model 9436 ) with a medium porosity glass fritt. The gas dispersion tube is held in an air tight fit with a ground glass joint screw adapter (Ace model 5028-25). The top of the gas dispersion tube may be fitted to plastic tubing carring nitrogen, solvents or liquid or gaseous reagents. Cooling to allow solvent reflux can be obtained by packing the fixed dispersion tubes in an insulated container of dry-ice. The reaction vessels may be sonicated, swirled on an orbital table, cooled in baths or heated in a high-temperature oil bath. Individual reactors can be opened, heated, or cooled, or left idle, on an individual basis as the need may arise, unlike block reactors described by DeWitt et al.

We claim:

1. A method of synthesizing 1, 4-piperazines and derivatives thereof comprising simultaneously cyclizing and cleaving an optionally substituted glycyl residue or dipeptoid from a polymeric support further comprising, prior to cyclization and cleavage, attaching an N-protected α-amino acid to a polymeric support; deprotecting said α-amino acid; reductively alkylating said α-amino acid with an aldehyde or ketone; bromoacetylating resulting secondary amine; and reacting resulting bromoacetyl compound with a primary amine.

2. The method according to claim 1 wherein said cyclization and cleavage is accomplished via heating in a non-reactive solvent in the presence of a catalyst.

3. The method according to claim 2 wherein said solvent is 2-butanol and said catalyst is acetic acid.

4. The method according to claim 1 wherein said α-amino acid is α-carbon substituted with benzyl, substituted benzyl, indole, methylnaphthyl, cyclohexyl, methylcyclohexyl, indanyl, (C1–C5) alkyloxyaryl, aminoalkyl (C1–C8), guanidino alkyl (C1–C8), alkylcarboxylic, hydroxyalkyl (C1–C5), alkylthioalkyl, (C1–C3) alkylbenzamidio or hydrogen.

5. The method according to claim 1 wherein said α-amino acid is selected from the group consisting of L- or D-Phenylanine, D- or L-Tryptophan, D- or l-Cyclohexylalanine, D- or L- β-2-Naphthylalanine, and D- or L-Indanylglycine.

6. The method according to claim 1 wherein said aldehyde is of the formula R1C(O)H, wherein R1 is cyclohexyl, methylcyclohexyl, benzyl, substituted benzyl, phenethyl, biphenyl, benzoyl, hydrogen, methylnapthyl, indanyl, guanidinoalkyl (C2–C8), aminoalkyl (C2–C8), arylalkylcarbamate with alkyl chains of C2 to C8, alkanoyl (C1–C12) or alkyl (C1–C12).

7. The method according to claim 1 wherein said aldehyde or ketone group is selected from the group consisting of cyclohexanone, cyclohexanone carboxaldehyde, benzaldehyde, phenylacetalaldehyde, 4'-biphenylcarboxaldehyde, 2-Napthaldehyde, 2-indanone-, 2-(N-Cbz)-ethanal, 6-(N-Cbz)-hexanal and 12-(N-Cbz)-dodecanal.

8. The method according to claim 1 wherein said primary amine is of the formula H2NR3 where R3 is selected from the group consisting of cyclohexyl, methylcyclohexyl, benzyl, substituted benzyl, phenethyl, biphenyl, benzoyl, hydrogen, methylnapthyl, indanyl, guanidinoalkyl (C2–C8), aminoalkyl (C2–C8), arylalkylcarbamates with alkyl chains of C2 to C8, alkanoyl (C1–C12), alkyl (C1–C12), (C2–C12) -alkylguanidinoalkyl (-C2–C8), benzamidino, (C1–C6) alkylbenzamidino, (C1–C6) alkylquinuclidine, (C1–C6) alkylpiperazine, C1 to C6 alkyl N-substituted piperazine, (C1–C6) alkylamino piperidine, (C1–C6) alkylamino N-substituted piperidine, (C1–C6) alkylcarboxyamidobenzamidino, (C1–C6) alkylcarboxamidoquinuclidine, (C1–C6) alkylcarboxamido piperazine, C1 to C6 alkylcarboxyl N-substituted piperazine, (C1–C6) alkylcarboxamidino piperidine and (C1–C6) alkylcarboxamidino N-substituted piperidine.

9. The method according to claim 1 wherein said primary amine is

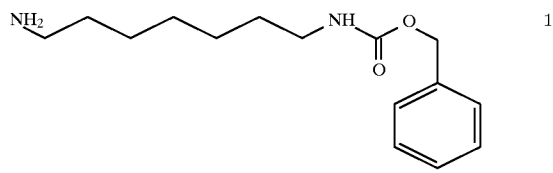

1

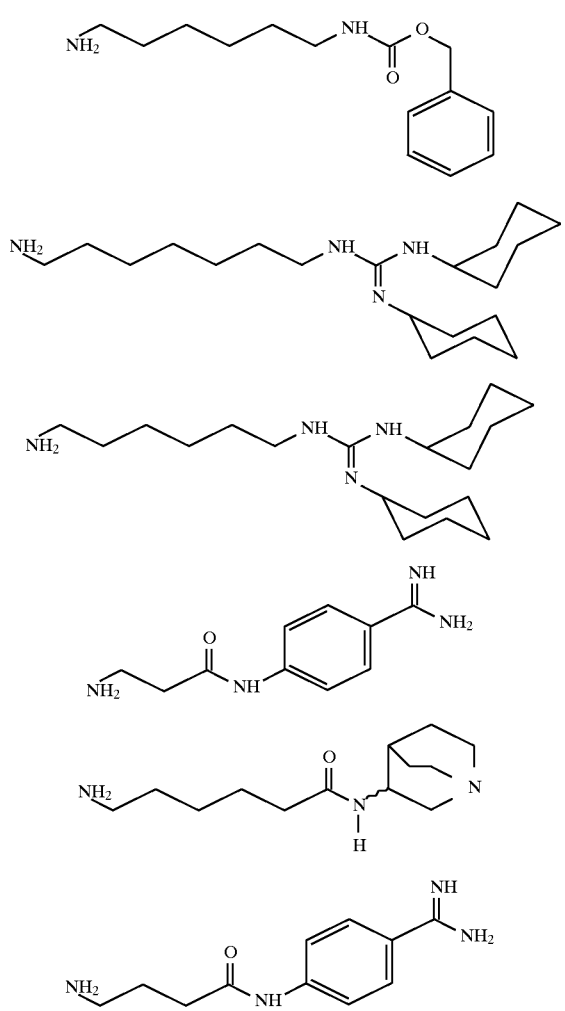
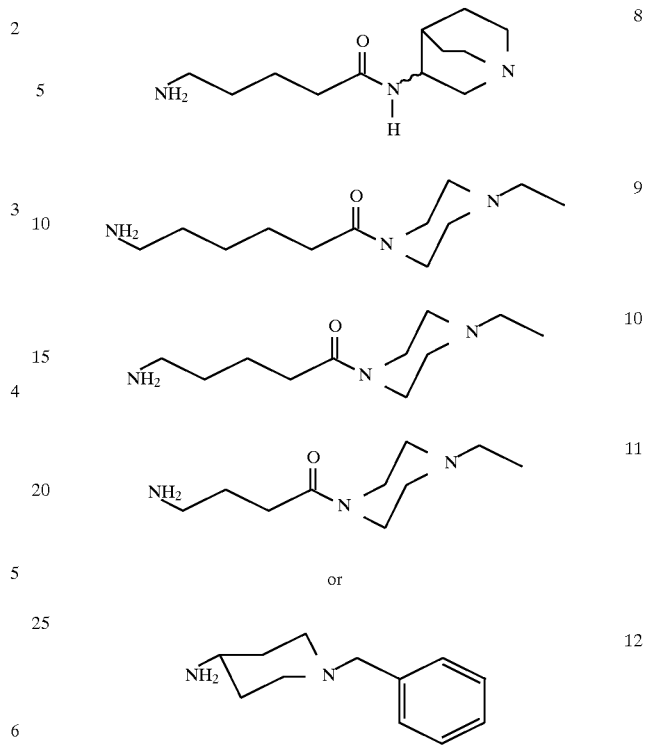
10. The method of synthesizing piperazines according to claim 1 further comprising reducing resulting 1,4-piperazine-2,5-dione.
11. The method according to claim 10 wherein said 1,4-piperazine-2,5-dione is reduced using diborane or lithium aluminum hydride.
* * * * *